United States Patent [19]

Kulagowski et al.

[11] Patent Number: 5,714,498
[45] Date of Patent: Feb. 3, 1998

[54] BENZIMIDAZOLE DERIVATIVES

[75] Inventors: Janusz Jozef Kulagowski, Bishops Stortford; Paul David Leeson, Cambridge, both of United Kingdom

[73] Assignee: Merck, Sharp, & Dohme, Ltd., Hertfordshire, England

[21] Appl. No.: 530,099

[22] PCT Filed: Mar. 16, 1994

[86] PCT No.: PCT/GB94/00528

§ 371 Date: Sep. 12, 1995

§ 102(e) Date: Sep. 12, 1995

[87] PCT Pub. No.: WO94/21615

PCT Pub. Date: Sep. 29, 1994

[30] Foreign Application Priority Data

Mar. 18, 1993 [GB] United Kingdom ............... 9305628
Aug. 5, 1993 [GB] United Kingdom ............... 9316258

[51] Int. Cl.$^6$ ............................. A61K 31/47; C07D 401/06
[52] U.S. Cl. ......................... 514/307; 514/322; 514/338; 514/394; 546/148; 546/199; 546/273.4; 548/305.1
[58] Field of Search .................... 546/199, 148, 546/273.4; 548/305.1; 514/322, 394, 307, 338

[56] References Cited

FOREIGN PATENT DOCUMENTS

| 0 034 249 A2 | 8/1981 | European Pat. Off. |
| 0 151 826 A1 | 8/1985 | European Pat. Off. |
| 0 411 631 A1 | 2/1991 | European Pat. Off. |
| 0 449 187 A2 | 10/1991 | European Pat. Off. |
| 1052718 | 2/1989 | Japan . |
| 24 32 519 A1 | 1/1975 | Netherlands . |

OTHER PUBLICATIONS

Derwent Abstract, JP-A-61-227565, 10-9-86, "Novel Piperidine Derivatives . . . ", Assignee Eisai KK Japan.

*Primary Examiner*—Joseph McKane
*Attorney, Agent, or Firm*—Robert J. North; Melvin Winokur

[57] ABSTRACT

The invention is directed to substituted benzimidazole compounds which are ligands for dopamine receptor subtypes used in the treatment of the dopamine system.

11 Claims, No Drawings

BENZIMIDAZOLE DERIVATIVES

This application is a 371 of PCT/6B/94/00528 filed Mar. 16, 1994.

This invention relates to a particular class of heteroaromatic compounds. More particularly, the invention is concerned with substituted benzimidazole derivatives which are ligands for dopamine receptor subtypes within the body and are therefore of use in the treatment and/or prevention of disorders of the dopamine system, including schizophrenia, depression, nausea, Parkinson's disease, tardive dyskinesias and extrapyramidal side-effects associated with treatment by conventional neuroleptic agents, neuroleptic malignant syndrome, and disorders of hypothalamic-pituitary function such as hyperprolactinaemia and amenorrhoea.

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

JP-A-61-227565 and JP-A-64-52718 describe in generic terms various [4-substituted-piperidin-1-yl-alkyl]-benzimidazole derivatives, which are stated to be effective against certain cardiovascular complaints. There is, however, no suggestion in either of these publications that the compounds described therein might be of any assistance in solving the problem of providing compounds which are ligands for dopamine receptor subtypes within the body and thus effective in the treatment and/or prevention of disorders of the dopamine system.

The compounds in accordance with the present invention, being ligands for dopamine receptor subtypes within the body, are accordingly of use in the treatment and/or prevention of disorders of the dopamine system.

The present invention accordingly provides a compound of formula I, or a salt or prodrug thereof:

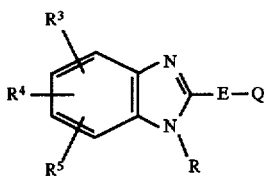

wherein
E represents —CH$_2$— or —CH$_2$CH$_2$—;
R represents hydrogen or C$_{1-6}$ alkyl;
Q represents a moiety of formula Qa, Qb or Qc:

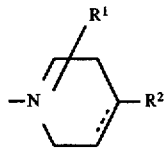

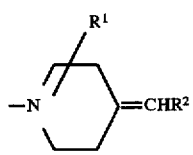

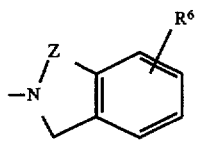

in which the broken line represents an optional chemical bond;

R$^1$ represents hydrogen, or an optionally substituted C$_{1-6}$ alkyl, C$_{1-6}$ alkoxy, C$_{2-6}$ alkenyl, C$_{2-6}$ alkynyl, aryl, aryl(C$_{1-6}$)alkyl, aryl(C$_{1-6}$)alkoxy, aryl(C$_{2-6}$)alkenyl, aryl(C$_{2-6}$)alkynyl, C$_{3-7}$ heterocycloalkyl(C$_{1-6}$)alkyl, heteroaryl, heteroaryl(C$_{1-6}$)alkyl, heteroaryl(C$_{2-6}$)alkenyl or heteroaryl (C$_{2-6}$)alkynyl group;

R$^2$ represents aryl, aryl(C$_{-6}$)alkyl, aryloxy(C$_{1-6}$)alkyl, aryl(C$_{1-6}$)alkyl, aryl(C$_{1-6}$)alkoxy, aryl(C$_{2-6}$)alkenyl, aryl (C$_{2-6}$)alkynyl, heteroaryl or heteroaryl(C$_{2-6}$)alkenyl, any of which groups may be optionally substituted on the aromatic moiety;

R$^3$, R$^4$ and R$^5$ independently represent hydrogen, hydrocarbon, a heterocyclic group, halogen, cyano, trifluoromethyl, nitro, —OR$^a$, -SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$;

Z represents —CH$_2$— or —CH$_2$CH$_2$—;

R$^6$ represents hydrogen, C$_{1-6}$ alkyl, C$_{1-6}$ alkoxy, aryl, aryl(C$_{1-6}$)alkyl or halogen; and R$^a$ and R$^b$ independently represent hydrogen, hydrocarbon or a heterocyclic group.

The present invention also provides compounds of formula I as defined above, and salts and prodrugs thereof, wherein R$^2$ is other than an aryloxy(C$_{1-6}$)alkyl group, optionally substituted on the aromatic moiety.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$ and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituent $R^1$ include straight-chained and branched alkenyl groups containing from 2 to 6 carbon atoms. Typical examples include vinyl and allyl groups.

Suitable alkynyl groups within the scope of the term "hydrocarbon" and within the definition of the substituent $R^1$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$, $R^2$ and $R^6$ include phenyl and naphthyl.

Particular aryl($C_{1-6}$)alkyl groups within the scope of the term "hydrocarbon" and within the definition of the substituents $R^1$, $R^2$ and $R^6$ include benzyl, naphthylmethyl, phenethyl and phenylpropyl.

A particular aryl($C_{2-6}$)alkenyl group within the scope of the term "hydrocarbon" and within the definition of the substituents $R^1$ and $R^2$ is phenylethenyl.

A particular aryl($C_{2-6}$)alkynyl group within the scope of the term "hydrocarbon" and within the definition of the substituents $R^1$ and $R^2$ is phenylethynyl.

Suitable heterocycloalkyl groups include azetidinyl, pyrrolidyl, piperidyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituent $R^1$ is tetrahydrofurylethyl.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, be-nzimidazolyl, oxadiazolyl and thiadiazolyl groups.

Particular heteroaryl($C_{1-6}$)alkyl groups within the scope of the expression "a heterocyclic group" and within the definition of the substituent $R^1$ include thienylmethyl, pyridylmethyl, pyrimidinylmethyl and pyrazinylmethyl.

Particular heteroaryl($C_{2-6}$)alkenyl groups within the scope of the expression "a heterocyclic group" and within the definition of the substituents $R^1$ and $R^2$ include furylethenyl and thienylethenyl.

The hydrocarbon and heterocyclic groups, as well as the substituents $R^1$ and $R^2$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyl oxy, —NR'R'', —NR''COR''', —NR''CO$_2$R''', —NR''SO$_2$R''', —CH$_2$NR''SO$_2$R''', —NHCONR'R''', —PO(OR') (OR'') —CONR'R''', —SO$_2$NR'R''' and —CH$_2$SO$_2$NR'R''', in which R' and R''' independently represent hydrogen, $C_{1-6}$ alkyl, aryl or aryl($C_{1-6}$)alkyl.

The term "halogen" as used herein includes fluorine, chlorine, bromine and iodine, especially chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof are encompassed within the scope of the present invention.

Suitably, the substituent R represents hydrogen or methyl, especially hydrogen.

Suitably, the substituent $R^1$ represents hydrogen.

As specified above, the substituent $R^2$ represents aryl, aryl($C_{1-6}$)alkyl, aryloxy($C_{1-6}$)alkyl, aryl($C_{1-6}$)alkoxy, aryl ($C_{2-6}$)alkenyl, aryl($C_{2-6}$)alkynyl, heteroaryl or heteroaryl ($C_{2-6}$)alkenyl, any of which groups may be optionally substituted on the aromatic moiety. Examples of optional substituents on the group $R^2$ include $C_{1-6}$ alkyl, halogen, trifluoromethyl, $C_{1-6}$ alkoxy, nitro, $C_{1-6}$ alkylamino and di($C_{1-6}$)alkylamino.

Particular values of $R^2$ include phenyl, chlorophenyl, ethylphenyl, methoxyphenyl, nitrophenyl, benzyl, chlorobenzyl, phenethyl, phenylpropyl, phenoxymethyl, benzyloxy, phenylethenyl, methoxyphenylethenyl, phenylethynyl, benzofuryl, benzthienyl, furylethenyl, methyl-furylethenyl and thienylethenyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{-6}$ alkyl, $C_{1-6}$ alkoxy, aryl($C_{1-6}$)alkoxy and $C_{2-6}$ alkylcarbonyl. Particular values include hydrogen, fluoro, chloro, methyl, ethyl, methoxy and benzyloxy.

Particular values of $R^6$ include hydrogen, phenyl, chloro and bromo.

One sub-class of compounds according to the invention is represented by the compounds of formula IIA, and salts and prodrugs thereof:

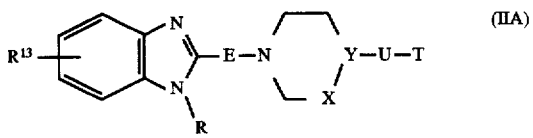
(IIA)

wherein

E and R are as defined with reference to formula I above;

U represents —(CH$_2$)$_n$—, —CH=CH— or —C≡C—;

n is zero, 1, 2 or 3;

—X—Y— represents —CH$_2$—CH— or —CH=C—;

T represents a group of formula (i), (ii), (iii), (iv), (v) or (vi):

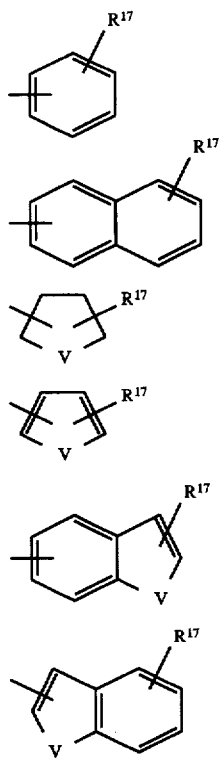

in which V represents oxygen, sulphur or NH; and $R^{13}$ and $R^{17}$ independently represent hydrogen, halogen, cyano, nitro, trifluoromethyl, amino, $C_{1-6}$ alkylamino, di($C_{-6}$)alkylamino, $C_{-6}$ alkyl, $C_{1-6}$ alkoxy, aryl($C_{1-6}$)alkoxy or $C_{2-6}$ alkylcarbonyl.

Particular values of $R^{13}$ include hydrogen, fluoro, chloro, methyl, ethyl, methoxy and benzyloxy.

Particular values of $R^{17}$ include hydrogen, chloro, methyl, methoxy and nitro.

Another sub-class of compounds according to the invention is represented by the compounds of formula IIB, and salts and prodrugs thereof:

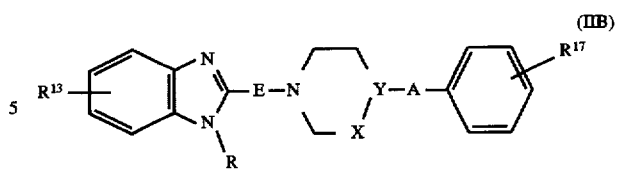
(IIB)

wherein

E and R are as defined with reference to formula I above;

A represents a moiety of formula —(CH$_2$)$_n$—, —CH=CH—, —C≡C—, —O—(CH$_2$)$_m$— or —(CH$_2$)$_m$—O—;

m is 1, 2 or 3; and n, X, Y, $R^{13}$ and $R^{17}$ are as defined with reference to formula IIA above.

In a subset of the compounds of formula IIB above, R represents hydrogen and A represents —C≡C—, —CH=CH— or —O—(CH$_2$)$_m$—.

A particular subset of the compounds of formula IIA and IIB as defined above is represented by the compounds of formula IIC, and salts and prodrugs thereof:

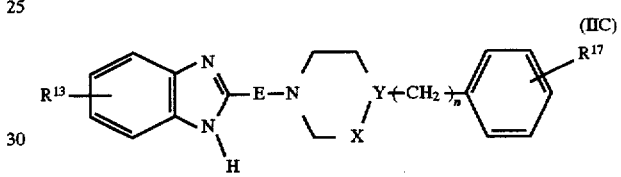
(IIC)

wherein

E is as defined with reference to formula I above; and n, X, Y, $R^{13}$ and $R^{17}$ are as defined with reference to formula IIA above.

A further sub-class of compounds according to the invention is represented by the compounds of formula IID, and salts and prodrugs thereof:

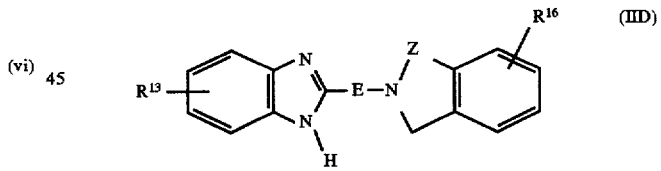
(IID)

wherein

E and Z are as defined with reference to formula I above;

$R^{13}$ is as defined with reference to formula IIA above; and $R^{16}$ represents hydrogen, $C_{1-6}$ alkyl, $C_{1-6}$ alkoxy, aryl, aryl($C_{1-6}$)alkyl or halogen.

Particular values of $R^{16}$ include hydrogen, phenyl, chloro and bromo, especially hydrogen.

A still further sub-class of compounds according to the invention is represented by the compounds of formula IIE, and salts and prodrugs thereof:

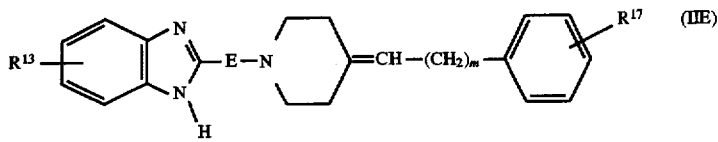

wherein

E is as defined with reference to formula I above;

$R^{13}$ and $R^{17}$ are as defined with reference to formula IIA above; and m is 1, 2 or 3.

Specific compounds within the scope of the present invention include:

2-(1,2,3,4-tetrahydroisoquinolin-2-ylmethyl)benzimidazole;

2-[4-(2-phenylethyl)piperidin-1-ylmethyl]benzimidazole;

2-(4-phenyl-1,2,3,6-tetrahydropyrid-1-ylmethyl)benzimidazole;

5-chloro-2-(1,2,3,4-tetrahydroisoquinolin-2-ylmethyl)benzimidazole;

5-methoxy-2-(1,2,3,4-tetrahydroisoquinolin-2-ylmethyl)benzimidazole;

2-(1,2-dihydroisoindol-2-ylmethyl)benzimidazole;

2-(4-benzylpiperidin-1-ylmethyl)benzimidazole;

2-(4-benzyl-1,2,3,6-tetrahydropyrid-1-ylmethyl)benzimidazole;

2-[4-(3-phenylpropyl)-1,2,3,6-tetrahydropyrid-1-ylmethyl]benzimidazole;

2-[4-(2-phenylethyl)-1,2,3,6-tetrahydropyrid-1-ylmethyl]benzimidazole;

2-[4-(2-phenylethynyl)-1,2,3,6-tetrahydropyrid-1-ylmethyl]benzimidazole;

2-(4-benzyloxy-1,2,3,6-tetrahydropyrid-1-ylmethyl)benzimidazole;

2-[4-(3-phenylpropyl)piperidin-1-ylmethyl]benzimidazole;

2-(4-benzyloxypiperidin-1-ylmethyl)benzimidazole;

2-[4-(3-phenylpropylidene)piperidin-1-ylmethyl]benzimidazole;

2-[4-(E)-(2-phenylethenyl)-1,2,3,6-tetrahydropyrid-1-ylmethyl]benzimidazole;

1-methyl-2-[4-(E)-(2-phenylethenyl)-1,2,3,6-tetrahydropyrid-1-ylmethyl]benzimidazole;

2-[4-(benzothiophen-2-yl)-1,2,3,6-tetrahydropyrid-1-ylmethyl]benzimidazole;

2-[4-(benzofuran-2-yl)-1,2,3,6-tetrahydropyrid-1-ylmethyl]benzimidazole;

2-[4-(E)-(2-(thien-2-yl)ethenyl)-1,2,3,6-tetrahydropyrid-1-ylmethyl]benzimidazole;

2-[4-(E)-(2-(thien-3-yl)ethenyl)-1,2,3,6-tetrahydropyrid-1-ylmethyl]benzimidazole;

2-[4-(E)-(2-(furan-2-yl)ethenyl)-1,2,3,6-tetrahydropyrid-1-ylmethyl]benzimidazole;

2-[4-(E)-(2-(5-methylfuran-2-yl)ethenyl)-1,2,3,6-tetrahydropyrid-1-ylmethyl]benzimidazole;

2-[4-(E)-(2-(3-methoxyphenyl)ethenyl)-1,2,3,6-tetrahydropyrid-1-ylmethyl]benzimidazole;

2-(4-phenoxymethyl-1,2,3,6-tetrahydropyrid-1-ylmethyl)benzimidazole; and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

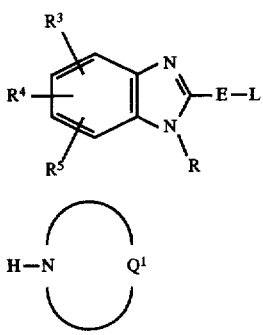

(III)

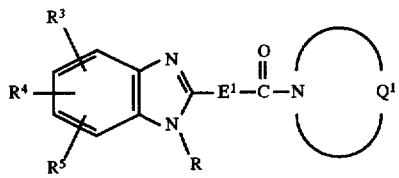

(IV)

wherein

E, R, R³, R⁴ and R⁵ are as defined above, Q¹ represents the residue of a moiety of formula Qa to Qc as defined above, and L represents a suitable leaving group.

The leaving group L is suitably a halogen atom, e.g. chlorine.

The reaction is conveniently carried out by stirring the reactants under basic conditions in a suitable solvent, for example potassium carbonate in N,N-dimethylformamide, or triethylamine in tetrahydrofuran or acetonitrile.

In an alternative procedure, the compounds in accordance with the present invention may be prepared by a process which comprises reducing a compound of formula V:

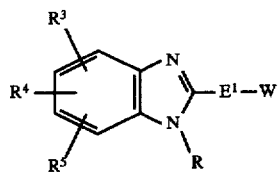

(V)

wherein

R, R³, R⁴, R⁵ and Q¹ are as defined above; and E¹ represents a bond or a methylene group.

The reaction is conveniently carried out by treating the compound V with a reducing agent such as lithium aluminium hydride in an appropriate solvent, e.g. tetrahydrofuran.

The intermediates of formula V above may suitably be prepared by reacting a compound of formula IV as defined above with a compound of formula VI:

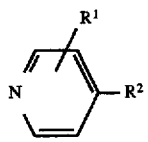

(VI)

wherein

R, R³, R⁴, R⁵ and E¹ are as defined above; and W represents a reactive carboxylate moiety.

Suitable values for the reactive carboxylate moiety W include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula VI above wherein W is an acid chloride moiety may be prepared by treating the corresponding carboxylic acid derivative with thionyl chloride in toluene. Similarly, the intermediates of formula VI wherein W is an acylimidazole moiety may be prepared by treating the corresponding carboxylic acid derivative with 1,1'-carbonyldiimidazole. Alternatively, the reactive carboxylate moiety W may be obtained by treating the corresponding compound wherein W is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula IV.

In a further procedure, the compounds according to the invention wherein Q represents a moiety of formula Qa in which the broken line represents a chemical bond may be prepared by a process which comprises reacting a compound of formula III as defined above with a compound of formula VII:

(VII)

wherein

R¹ and R² are as defined above; followed by treatment of the resulting pyridinium salt with a reducing agent.

Reduction of the pyridinium salt is conveniently brought about by treatment with sodium borohydride in ethanol.

Where they are not commercially available, the starting materials of formula III, IV, VI and VII may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile. Moreover, a compound of formula I wherein Q represents a moiety of formula Qa in which the broken line represents a chemical bond initially obtained may be converted into the corresponding compound in which the broken line is absent suitably by conventional catalytic hydrogenation techniques.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.

W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

2-(4-[2-Phenylethyl]piperidin-1-ylmethyl) benzimidazole 2-(Chloromethyl)benzimidazole (448 mg, 2.64 mmol) and potassium carbonate (729 mg, 5.28 mmol) were added to a solution of 4-(2-phenylethyl)piperidine (500 mg, 2.64 mmol) in dry DMF (20 ml) under a nitrogen atmosphere and the mixture stirred at room temperature for 20 hours. The reaction was diluted with water (200 ml) and extracted with ethyl acetate (3×100 ml), the combined organic layers were washed with water (25 ml) and brine (50 ml), dried ($MgSO_4$) and evaporated in vacuo to give a brown oil which was triturated with toluene and recrystallised from methanol to give the title compound as a sandy solid (97.3 mg, 12%). m.p. 170° C.; (Found: C, 78.38; H, 7.79; N, 12.93. $C_{21}H_{25}N_3.0.1$ $H_2O$ requires C, 78.51; H, 7.91; N, 13.08%); $\delta_H$ (DMSO-$d_6$) 1.22 (3H, m, piperidinyl H and $CH_2CH_2Ph$), 1.50 (2H, m, piperidinyl $CH_2$), 1.67 (2H, m, piperidinyl $CH_2$), 2.01 (2H, m, piperidinyl $CH_2$), 2.56-2.60 (2H, m, piperidinyl $CH_2$), 2.83 (2H, d, J 10.8Hz, $CH_2$-Ph), 3.67 (2H, s, N-$CH_2Ar$), 7.12-7.19 (5H, m, ArH), 7.24-7.28 (2H, m, ArH), 7.42 (1H, d, J 7.3 Hz, ArH), 7.53 (1H, d, 3 7.3Hz, ArH), and 12.20 (1H, brs, NH); m/z (CI$^+$, NH$_3$) 320 (M+1)$^+$.

Prepared in an analogous way were:

EXAMPLE 2

2-(1,2,3,4-Tetrahydroisoquinolin-2-ylmethyl) benzimidazole

M.p. 184°–186° C. (EtOAc); (Found: C, 76.60; H, 6.47, N, 15.76. $C_{17}H_{17}N_3.0.2H_2O$ requires C, 76.49; H, 6.57; N, 15.74%); $\delta_H$ (DMSO-$d_6$) 2.50 (2H, t, J 1.8 Hz, $CH_2$), 2.78 (2H, m, $CH_2$), 2.86 (2H, t, J 5.8 Hz, $CH_2$), 3.65 (2H, s, N—$CH_2$), 3.90 (2H, s, N-$CH_2$), 7.01-7.17 (6H, m, ArH), 7.42 (1H, d, J 6.8 Hz, ArH), 7.56 (1H, d, J 9.1 Hz, ArH), and 12.32 (1H, brs, NH); m/z (CI$^+$, NH$_3$) 264 (M+1)$^+$.

EXAMPLE 3

2-(4-Phenyl-1,2,3,6-tetrahydropyridin-1-ylmethyl) benzimidazole

M.p. 253°–255° C. (MeOH); (Found: C, 77.72; H, 6.47; N, 14.48. $C_{19}H_{19}N_3.0.25H_2O$ requires C, 77.65; H, 6.69; N, 14.30%); $\delta_H$ (DMSO-$d_6$) 2.82 (2H, brs, $CH_2$), 3.55 (2H, brs, $CH_2$), 4.01 (2H, brs, $CH_2$), 4.71 (2H, brs, $CH_2$-N), 6.21 (1H, brs, CH), 7.29-7.48 (5H, m, ArH), 7.48-7.51 (2H, m, ArH), 7.68-7.73 (2H, m, ArH), and 11.81 (1H, brs, NH); m/z (CI$^+$, NH$_3$) 290 (M+1)$^+$.

EXAMPLE 4

2-(4-Benzylpiperidin-1-ylmethyl)benzimidazole

M.p. 179°–181° C. (PhMe); (Found: C, 78.23; H, 7.36; N, 13.53; $C_{20}H_{23}N_3$ requires C, 78.65; H, 7.59; N, 13.76%); $\delta_H$ (CDCl$_3$) 1.27-1.38 (2H, m, piperidinyl H), 1.53-1.67 (3H, m, piperidinyl H), 2.13 (2H, t, J 11.8 Hz, piperidinyl H), 2.55 (2H, d, J 6.8 Hz, Ph$CH_2$CH), 2.87 (2H, d, J 11.7 Hz, piperidinyl H), 3.78 (2H, s, N$CH_2$Ar), 7.12-7.29 (9H, m, ArH), and 7.49 (1H, brs, NH); m/z (CI$^+$, NH$_3$) 306 (M+1)$^+$.

EXAMPLE 5

2-(1,2-Dihydroisoindol-2-ylmethyl)benzimidazole

M.p. 172°–174° C. (PhMe); (Found: C, 77.10; H, 5.99, N, 16.89; $C_{16}H_{15}N_3$ requires C, 77.08; H, 6.06; N, 16.85%); $\delta_H$ (CDCl$_3$) 4.05 (4H, s, isoindolinyl H), 4.24 (2H, s, N$CH_2$Ar), 7.15-7.25 (8H, m, ArH), and 7.53 (1H, brs, NH); m/z (CI$^+$, NH$_3$) 250 (M+1)$^+$.

EXAMPLE 6

5-Chloro-2-(1,2,3,4-tetrahydroisoquinolin-2-ylmethyl)benzimidazole

M.p. 204°–206° C. (PhMe); C, 68.38; H, 5.25; N, 13.92. $C_{19}H_{16}ClN_3$ requires C, 68.57; H, 5.42; N, 14.11%); $\delta_H$ (CDCl$_3$) 2.99-3.03 (4H, m, 2×tetrahydroisoquinolyl $CH_2$), 3.85 (2H, s, tetrahydroisoquinolyl $CH_2$), 4.13 (2H, s, N$CH_2$Ar), 7.00 (1H, d, J 8.6 Hz, ArH), 7.12-7.26 (5H, m, ArH), 7.49 (1H, d, J 12.3 Hz, ArH), and 7.57 (1H, brs, NE); m/z (CI$^+$, NH$_3$) 298 (M+1)$^+$.

EXAMPLE 7

5-Methoxy-2-(1,2,3,4-tetrahydroisoquinolin-2-ylmethyl)benzimidazole dihydrochloride M.p. 212°–215° C. (MeOH/Et$_2$O); (Found: C, 59.14; H, 5.69; N, 11.13. $C_{18}H_{19}N_3O.2HCl$ requires C, 59.02; H, 5.7.7; N, 11.47%); $\delta_H$ (DMSO-$d_6$) 3.13 (2H, brs, tetrahydroisoquinolyl $CH_2$), 3.53 (2H, brs, tetrahydroisoquinolyl $CH_2$), 3.84 (3H, s, OCH$_3$), 4.44 (2H, brs, tetrahydroisoquinolyl $CH_2$), 4.71 (2H, s, N$CH_2$Ar), 7.04 (1H, dd, J 9.0, 2.3 Hz, ArH), 7.16-7.27 (5H, m, ArH), and 7.65 (1H, d, J 9.0 Hz, ArH); m/z (CI$^+$, NH$_3$), 294 (M+1)$^+$.

EXAMPLE 8

2-(4-[$^3$-Phenylpropyl]-1,2,3,6-tetrahydropyridin-1-ylmethyl)benzimidazole

A mixture of 2-(chloromethyl)benzimidazole (2.48 g, 14.9 mmol) and 4-(3-phenylpropyl)pyridine (15 ml) was stirred at 140° C. under a nitrogen atmosphere for ten minutes. The reaction mixture was allowed to cool and the resultant solid triturated with acetonitrile (10 ml). The mixture was diluted with ethyl acetate (10 ml), the solid collected by filtration and washed with acetonitrile/ethyl acetate to afford the intermediate pyridininm salt (4.85 g, 85%), as a tan solid.

A portion of this solid (2.51 g, 6.90 mmol) was dissolved in ethanol (70 ml) and sodium borohydride (1.04 g, 27.5 mmol) added portionwise to the solution over a five minute period. The reaction mixture was stirred at room temperature under a nitrogen atmosphere for thirty minutes followed by addition of acetic acid (approx. 3 ml) and further stirring for ten minutes. The precipitated solid was collected and the filtrate concentrated in vacuo. Saturated aqueous potassium carbonate (100 ml) was added to the residue and the mixture extracted with ethyl acetate (2×100 ml). The extracts were washed with brine (50 ml), combined, dried (MgSO$_4$) and evaporated to an amber oil which crystallised on standing. Recrystallisation from ethyl acetate gave the title compound (1.52 g, 66%) as a white crystalline solid, m.p. 131°–132° C.; (Found: C, 79.85; H, 7.78; N, 12.71. C$_{22}$H$_{25}$N$_3$ requires C, 79.72; H, 7.60; N, 12.68%); $\delta_H$ (DMSO-d$_6$) 1.67 (2H, m, CH$_2$CH$_2$CH$_2$Ph), 1.96 (2H, t, J 7.8 Hz, CH$_2$CH$_2$CH$_2$Ph), 2.04 (2H, br s, tetrahydropyridinyl CH$_2$), 2.56 (4H, m, CH$_2$CH$_2$CH$_2$Ph and tetrahydropyridinyl CH$_2$), 2.96 (2H, br s, tetrahydropyridinyl CH$_2$), 3.76 (2H, s, N-CH$_2$Ar), 5.37 (1H, br s, —CH=), 7.14 (5H, m, ArH), 7.27 (2H, m, ArH), 7.42 (1H, d, J 7 Hz, ArH), 7.54 (1H, d, J 7 Hz, ArH), and 12.28 (1H, br s, NH); m/z (CI$^+$, NH$_3$) 332 (M+1)$^+$.

Prepared in an analogous manner was:

EXAMPLE 9

2-(4-Phenylmethyl-1,2,3,6,-tetrahydropyridin-1-ylmethyl)benzimidazole

M.p. 177°–178° C. (dec.) (EtOAc); (Found: C, 79.18; H, 6.72; N, 13.54. C$_{20}$H$_{21}$N$_3$ requires C, 79.17; H, 6.98; N, 13.85%); $\delta_H$ (DMSO-d$_6$) 1.98 (2 H, br s, tetrahydropyridinyl CH$_2$), 2.54 (2H, t, J 5.7 Hz, tetrahydropyridinyl CH$_2$), 3.26 (2H, s, CH$_2$Ph), 3.75 (2H, s, N-CH$_2$Ar), 5.42 (1H, br s, CH=CR), 7.16 (5H, m, ArH), 7.27 (2H, m, ArH), 7.40 (1H, br d, J 6.9 Hz, ArH), 7.53 (1H, br d, J 6.9 Hz, ArH), and 12.26 (1H, br s, NH); m/z (CI$^+$, NH$_3$) 304 (M+1)$^+$.

EXAMPLE 10

2-(4-[2-Phenylethyl]-1,2,3,6-tetrahydropyridin-1-ylmethyl)benzimidazole

M.p. 177°–179° C. (PhMe); (Found: C, 79.54; H, 7.19; N, 13.07. C$_{21}$H$_{23}$N$_3$ requires C, 79.56; H, 7.30; N, 13.24%); $\delta_H$ (CDCl$_3$) 2.18 (2H, br s, CH$_2$), 2.28-2.32 (2H, m, CH$_2$), 2.69-2.76 (4H, m, 2 x CH$_2$), 3.09 (2H, br s, CH$_2$), 3.91 (2H, s, ArCH$_2$N), 5.42 (1H, br s, CH=CR), 7.17-7.31 (5H, m, ArH), and 7.57 (2H, br s, ArH+NH); m/z (CI$^+$, NH$_3$) 318 (M+1)$^+$.

EXAMPLE 11

2-(4-[2-Phenylethynyl]-1,2,3,6-tetrahydropyridin-1-ylmethyl)benzimidazole dihydrochloride M.p. 244° C. (dec.) (MeOH/Et$_2$O); (Found: C, 64.96; H, 5.47; N, 11.28. C$_{21}$H$_{21}$Cl$_2$N$_3$ requires C, 65.29; H, 5.48; N, 10.88%); $\delta_H$ (DMSO-d$_6$) 2.60 (2H, br s, CH$_2$), 3.37-3.39 (2H, m, CH$_2$), 3.88 (2H, br s, CH$_2$), 4.65 (2H, s, CH$_2$N), 6.20 (1H, s, CH=CR), 7.39-7.47 (7H, m, ArH), and 7.73-7.76 (2H, m, ArH); m/z (CI$^+$, NH$_a$) 314 (M+1)$^+$.

EXAMPLE 12

2-(4-Benzyloxy-1,2,3,6-tetrahydropyridin-1-ylmethyl)benzimidazole

Step 1: 4-Benzyloxypyridine

To a suspension of sodium hydride (80% dispersed in oil, 876 mg, 29.2 mmol) in DMSO (10 ml) was added benzyl alcohol (3 ml, 29.2 mmol) and the mixture stirred at room temperature for 1 hour. To this was added 4-chloropyridine (3.3 g, 29.2 mmol) and the reaction stirred at room temperature overnight. The precipitated sodium chloride was removed by filtration and the filtrate diluted with water (100 ml) and extracted with ether (3×120 ml). The combined organic layers were dried (MgSO$_4$) and evaporated in vacuo to yield the title compound as an oil (4.8 g, 95%); $\delta_H$ (CDCl$_3$) 5.11 (2H, s, PhCH$_2$O), 6.87 (2H, d, J 6.3 Hz, 3-H, 5-H), 7.29-7.42 (5H, m, Ph), and 8.42 (2H, d, J 6.3 Hz, 2-H, 6-H).

Step 2: 2-(4-Benzyloxy-1,2,3,6-tetrahydropyridin-1-ylmethyl)benzimidazole

Prepared from 4-benzyloxy pyridine and 2-(chloromethyl) benzimidazole in an analagous manner to that described previously. M.p. 170°–172° C. (PhMe); (Found: C, 75.19; H, 6.45; N, 13.02. C$_{20}$H$_{21}$N$_3$O requires C, 75.21; H, 6.63; N, 13.16%). $\delta_H$ (CDCl$_3$) 2.35 (2H, br s, tetrahydropyridinyl 3-CH$_2$), 2.81 (2H, t, J 5.6 Hz, tetrahydropyridinyl 2-CH$_2$), 3.21 (2H, br s, tetrahydropyridinyl 6-CH$_2$), 3.98 (2H, s, NCH$_2$Ar), 4.75 (1H, br s, tetrahydropyridinyl 5-CH), 4.81 (2H, s, PhCH$_2$O), 7.22-7.27 (3H, m, ArH), 7.31-7.37 (6H, m, ArH), and 7.56 (1H, br s, NH); m/z (CI$^+$, NH$_3$), 336 (M+NH$_4$)$^+$.

EXAMPLE 13

2-(4-[3-Phenylpropyl]piperidin-1-ylmethyl) benzimidazole

A mixture of 2-(4-[3-phenylpropyl]-1,2,3,6-tetrahydropyridin-1-ylmethyl)benzimidazole (1.01 g, 3.05 mmol) and platinum (IV) oxide hydrate (56 mg) in ethyl acetate (75 ml) was hydrogenated on a Parr apparatus (30 psi maximum) for 70 minutes. Fresh catalyst was added (40 mg) and the mixture hydrogenated for a further 2.5 h. The mixture was filtered and evaporated to dryness. Flash chromatography eluting with 7.5% methanol in dichloromethane followed by recrystallisation from ethyl acetate/petrol (60°–80° C.) gave the title compound (0.52 g, 52%) as a white solid, m.p. 140°–141° C.; (Found: C, 79.25; H, 8.07; N, 12.39. C$_{22}$H$_{27}$N$_3$ requires C, 79.24; H, 8.16; N, 12.60%); $\delta_H$ (DMSO-d$_6$) 1.19 (5H, m, 2×CH$_2$+piperidinyl CH), 1.57 (4H, m, 2×CH$_2$), 2.02 (2H, m, CH$_2$), 2.55 (2H, m, piperidinyl CH$_2$), 2.81 (2H, m, piperidinyl CH$_2$), 3.66 (2H, s, CH$_2$N), 7.15 (5H, m, ArH), 7.26 (2H, m, ArH), 7.43 (1H, br d, ArH), 7.51 (1H, br d, ArH), and 12.16 (1H, br s, N$_3$H); m/z (CI$^+$, NH$_3$) 334 (M+1)$^+$.

EXAMPLE 14

2-(4-Benzyloxypiperidin-1-ylmethyl)benzimidazole

Step 1: 1-(tert-Butoxycarbonyl)-4-benzyloxypiperidine

Sodium hydride, 80% dispersion in oil (0.14 g, 4.8 mmol) was added to a solution of 1-(tert-butoxycarbonyl)-4-hydroxypiperidine (1.0 g, 4.8 mmol) [prepared from 4-hydroxypiperidine and di-tert-butyl dicarbonate] in dimethylformamide (30 ml) and the mixture stirred for 30 minutes. Benzyl bromide (0.68 ml, 5.7 mmol) was added and the reaction mixture stirred overnight. The mixture was poured into water and extracted with dichloromethane. The extracts were washed with water and brine, dried (MgSO$_4$) and the residue after evaporation purified by flash chromatography eluting with 0–20% ethyl acetate in hexane to give 1-(tert-butoxycarbonyl)-4-benzyloxypiperidine (1.1 g, 94%); δ$_H$ (CDCl$_3$) 1.39 (9H, s, C(CH$_3$)$_3$), 1.82 (2H, m, piperidinyl. H), 3.04 (2H, m, piperidinyl H), 3.59 (3H, m, piperidinyl H), 4.51 (2H, s, OCH$_2$Ph), 7.24-7.39 (5H, m, PhH).

Step 2: 2-(4-Benzyloxynipepidin-1-ylmethyl) benzimidazole

Trifluoroacetic acid (5 ml) was added to a solution of 1-(tert-butoxycarbonyl)-4-benzyloxypiperidine (2.08 g, 7.14 mmol) in dichloromethane (20 ml) and the solution stirred for 30 minutes at room temperature under nitrogen. The solution was concentrated in vacuo, the residue was redissolved in dichloromethane (20 ml) and treated with trifluoroacetic acid (20 ml). The solution was stirred for 30 minutes, partially evaporated and poured into saturated aqueous potassium carbonate solution (50 ml). The mixture was diluted with water (50 ml) and extracted with dichloromethane (2×100 ml). The combined extracts were dried (MgSO$_4$) and concentrated in vacuo to give crude 4-benzyloxypiperidine (1.29 g), as an amber oil. A portion of this material (0.59 g, 3.08 mmol) was dissolved in dimethylformamide (15 ml). Potassium carbonate (0.85 g, 6.15 mmol) and 2-(chloromethyl) benzimidazole (0.46 g, 2.76 mmol) were added to the solution and the mixture stirred at room temperature, under nitrogen, overnight. The reaction mixture was poured into water (150 ml) and extracted with ethyl acetate (2×100 ml). The extracts were washed with brine (100 ml), combined, dried (MgSO$_4$) and the residue after evaporation purified by flash chromatography, eluting with 7.5% methanol in dichloromethane, to give the title compound (0.26 g, 30%) as a pale yellow solid. Recrystallisation from ethyl acetate afforded very pale yellow needles, m.p. 190.5°–191° C.; (Found: C, 74.83; H, 7.17; N, 13.00. C$_{20}$H$_{23}$N$_3$O requires C, 74.74; H, 7.21; N, 13.07%); δ$_H$ (DMSO-d$_6$) 1.56 (2H, m, piperidinyl H), 1.88 (2H, m, piperidinyl H), 2.21 (2H, m, piperidinyl H), 2.74 (2H, m, piperidinyl H), 3.40 (1H, m, piperidinyl CH-O), 3.69 (2H, s, CH$_2$N), 4.49 (2H, s, OCH$_2$Ph), 7.12 (2H, m, ArH), 7.27 (5H, m, ArH), 7.48 (2H, br s, ArH), and 12.23 (1H, br s, NH); m/z (CI$^+$, NH$_3$) 322 (M+H)$^+$.

EXAMPLE 15

2-(4-[3-Phenylpropylidene]piperidin-1-ylmethyl) benzimidazole

Step 1: 4-(3-Phenylpropylidene)piperidine n-Butyl lithium (2.5M in hexanes, 14 ml, 35 mmol) was carefully added to a cold (<0° C.) suspension of 3-phenylpropyltriphenylphosphonium bromide (18.7 g, 40.5 mmol) in THF (100 ml) under a nitrogen atmosphere at such a rate that the temperature did not exceed 0° C. The orange solution was stirred at <0° C. for 30 minutes before a solution of 1-(tert-butyloxycarbonyl)-4-piperidone (5.0 g, 27 mmol) was added as a solution in THF (20 ml) at such a rate that the temperature did not exceed 0° C. The mixture was stirred at 0° C. for 1 hour and then allowed to warm to room temperature before adding water (20 ml). The mixture was concentrated in vacuo and the residue extracted into dichloromethane (3×100 ml). The combined organics were washed with water (20 ml) and brine (20 ml), dried (MgSO$_4$) and evaporated in vacuo to give a yellow oil. The oil was purified by column chromatography on silica eluting with 10% EtOAc/petrol 60/80 to give a clear oil. The oil was dissolved in dichloromethane (30 ml) and treated with trifluoroacetic acid (20 ml) and the mixture stirred at room temperature for 1.5 h. The solution was evaporated in vacuo and azeotroped with toluene (2×10 ml). The residue was dissolved in EtOAc (20 ml) and washed with sodium carbonate (saturated, 2×10 ml), water (10 ml) and brine (10 ml), dried (MgSO$_4$) and evaporated in vacuo to give 4-(3-phenylpropylidene) piperidine as a pale oily solid (4.92 g, 90%).

Step 2: 2-(4-[3-Phenylpropylidene]piperidin-1-ylmethyl) benzimidazole

Prepared as described before, m.p. 163°–165° C. (EtOAc); (Found: C, 79.99; H, 7.52; N, 12.67. C$_{22}$H$_{25}$N$_3$ requires C, 79.72; H, 7.60; N, 12.68%); δ$_H$ (CDCl$_3$) 2.17-2.23 (4H, m, 2×piperidinyl CH$_2$), 2.28-2.38 (4H, m, aliphatic H), 2.51 (2H, t, J 5.6 Hz, aliphatic H), 2.64 (2H, t, J 7.5 Hz, CH$_2$CH$_2$Ph), 3.79 (2H, s, CH$_2$-N), 5.21 (1H, t, J 7.3 Hz, C=CH), 7.14-7.21 (3H, m, ArH), 7.22-7.28 (4H, m, ArH), and 7.40-7.60 (2H, br s, ArH); m/z (CI$^+$, NH$_3$) 332 (M+1)$^+$.

EXAMPLE 16

(E)-2-(4-[2-Phenylethenyl]-1,2,3,6-tetrahydropyridin-1-ylmethyl)benzimidazole

A solution of 4-styrylpyridine (4.0 g, 22.1 mmol) and 2-chloromethylbenzimidazole (3.7 g, 22.1 mmol) in dimethylformamide (20 ml) was heated at 110°–120° C. under a nitrogen atmosphere for 1.5 hours. The mixture was cooled to room temperature, diluted with ethanol (380 ml) and carefully treated with sodium borohydride (880 mg, 23.2 mmol). The mixture was stirred at room temperature for 2 hours, then heated at reflux for 1 hour before stirring at room temperature overnight. The ethanol was evaporated in vacuo and the residue partitioned between ethyl acetate (100 ml) and sodium carbonate (half saturated, 100 ml). The phases were separated and the aqueous was extracted with ethyl acetate (2×100 ml). The combined organics were washed with water (50 ml) and brine (50 ml), dried (MgSO$_4$) and evaporated in vacuo to give a reddish gummy residue which was purified by flash chromatography (eluting with 5% methanol in dichloromethane) to give a yellow gummy solid. The gum was triturated with ethyl acetate and recrystallised from ethyl acetate to give the title compound as a mustard solid (912 mg, 13%). M.p. 225°–227° C. (EtOAc); (Found: C, 79.74; H, 6.89; N, 13.47. C$_{21}$H$_{21}$N$_3$ requires C, 79.97; H, 6.71; N, 13.32%); δ$_H$ (DMSO-d$_6$) 2.37 (2H, br s, tetrahydropyridinyl CH$_2$), 2.69 (2H, t, J 5.6 Hz, tetrahydropyridinyl CH$_2$), 3.17 (2H, br s, tetrahydropyridinyl CH$_2$), 3.83 (2H, s, NCH$_2$Ar), 5.91 (1H, s, CH=CR), 6.48 (1H, d, J 16.2 Hz, CHCHPh), 6.91 (1H, d, J-16.2 Hz, CHPh), 7.13-7.22 (3H, m, ArH), 7.29-7.33 (2H, m, ArH), 7.42-7.47 (3H, m, ArH), 7.54 (1H, m, ArH), and 12.31 (1H, br s, NH); m/z (CI$^+$, NHs) 316 (M+1)$^+$.

EXAMPLE 17

1-Methyl-2-(4-(E)-2-phenylethenyl-1,2,3,6-tetrahydropyridin-1-ylmethyl)benzimidazole The title compound was prepared by treatment of 2-chloromethyl-1-methylbenzimidazole (prepared using the procedure of M. A. Phillips, J. Chem. Soc., 1928, 2393) in a manner analogous to Example 16.

M.p. 188°–190° C. (MeOH/Et$_2$O); (Found: C, 58.69; H, 6.50; N, 9.15. C$_{22}$H$_{23}$N$_3$.2HCl.2.5H$_2$O requires C, 59.06; H, 6.76; N, 9.39%); δ$_H$ (DMSO-d$_6$) 2.45-2.56 (2H, m, tetrahydropyridinyl CH$_2$), 2.72 (2H, m, tetrahydropyridinyl CH$_2$), 4.01 (3H, s, CH$_3$), 4.08 (2H, br s, tetrahydropyridinyl CH$_2$), 4.83 (2H, s, NCH$_2$Ar), 5.94 (1H, br s, tetrahydropyridinyl CH=CR), 6.63 (1H, d, J 16.3 Hz, CH=CH-Ph), 6.99 (1H, d, J 16.3 Hz, CH=CH-Ph), 7.23-7.53 (7H, m, ArH), and 7.77 (2H, d, J 7.7 Hz, ArH); m/z (CI$^+$, NH$_3$) 330 (M+1)$^+$.

EXAMPLE 18

2-(4-[Benzothiophen-2-yl]-1,2,3,6-tetrahydropyridin-1-ylmethyl)benzimidazole

Step 1: 1-Benzyl-4-(benzothiophen-2-yl)-1,2,3,6-tetrahydropyridine

To a solution of benzothiophene (3 g, 22.4 mmol) in anhydrous tetrahydrofuran (50 ml) at –10° C. under nitrogen was added n-butyllithium (9.83 ml of a 2.5M solution in toluene), the mixture was left to warm to room temperature and stirred for 1 hr. The reaction mixture was cooled to –40° C., 1-benzyl-4-piperidone (4.23 g, 22.4 mmol) added, the mixture left to warm to room temperature and stirred for 14 hr. The reaction mixture was concentrated in vacuo and trifluoroacetic acid (10 ml) added. This mixture was stirred at room temperature for 14 hr then concentrated in vacuo. The product was extracted into dichloromethane (3×100 ml) from aqueous potassium carbonate. The organic layer was washed with water (1×50 ml), brine (1×50 ml), then dried (MgSO$_4$). After concentration of the extracts the crude product was purified using silica gel column chromatography to yield the title compound (4.2 g, 68%) as a colourless oil; δ$_H$ (CDCl$_3$) 2.64 (2H, m, tetrahydropyridinyl CH$_2$), 2.74 (2H, m, tetrahydropyridinyl CH$_2$), 3.18 (2H, m, tetrahydropyridinyl CH$_2$), 3.65 (2H, s, PhCH$_2$N), 6.18 (1H, m, CH=C), 7.11 (1H, s, benzothiophene 3-H), and 7.24-7.73 (9H, m, ArH).

Step 2: 4-(Benzothiophen-2-yl)-1,2,3,6-tetrahydropyridine hydrochloride

To a solution of 1-benzyl-4-(benzothiophen-2-yl)-1,2,3,6-tetrahydropyridine (4 g, 13.1 mmol) in anhydrous dichloromethane (50 ml) at 0° C. under nitrogen was added 2-chloroethylchloroformate (1.84 ml, 17.0 mmol) and the mixture stirred for 1 hr. The reaction mixture was concentrated in vacuo, methanol (20 ml) added and heated to reflux for 1 hr. After cooling the title compound was collected by filtration (2.2 g, 67%), m.p. 269° C. (dec.).

Step 3: 2-(4-Benzothiophen-2-yl)-1,2,3,6-tetrahydropyridin-1-ylmethyl)benzimidazole The title compound was prepared in a analogous manner to Example 1 using 4-(benzothiophen-2-yl)-1,2,3,6-tetrahydropyridine hydrochloride and 2-chloromethylbenzimidazole, m.p. 241° C. (dec.); (Found: C, 72.44; H, 5.41; N, 11.83. C$_{12}$H$_{19}$N$_3$S.0.1H$_2$O requires C, 72.63; H, 5.57; N, 2.10%); δ$_H$ (DMSO-d$_6$) 2.62 (2H, br s, tetrahydropyridinyl CH$_2$), 2.77 (2H, m, tetrahydropyridinyl CH$_2$), 3.24 (2H, d, J 2.8 Hz, tetrahydropyridinyl CH$_2$), 3.87 (2H, s, NCH$_2$Ar), 6.23 (1H, br s, CH=CR), 7.10-7.42 (1H, m, ArH), 7.45 (1H, d, J 8 Hz, ArH), 7.74 (1H, d, J 8 Hz, ArH), 7.76 (1H, dd, J 8, 2 Hz, ArH), 7.86 (1H, dd, J 8, 2 Hz, ArH), and 12.32 (1H, br s, NH); m/z (CI$^+$, NH$_3$) 346 (M+1)$^+$.

EXAMPLE 19

2-(4-[Benzofuran-2-yl]-1,2,3,6-tetrahydropyridin-1-ylmethyl)benzimidazole

M.p. 202°–204° C. (PhMe); (Found: C, 76.45; H, 5.51; N, 11.73. C$_{21}$H$_{19}$N$_3$O requires C, 76.58; H, 5.81; N, 12.76%); δ$_H$ (DMSO-d$_6$) 2.59 (2H, br s, tetrahydropyridinyl CH$_2$), 2.85 (2H, t, J 5.7 Hz, tetrahydropyridinyl CH$_2$), 3.35 (2H, br s., tetrahydropyridinyl CH$_2$), 3.99 (2H, s, NCH$_2$Ar), 6.50 (1H, br s, tetrahydropyridinyl 5—CH), 6.56 (1H, s, 2'-H), 7.16-7.27 (6H, m, ArH), 7.43 (1H, d, J 7.9 Hz, ArH), 7.52 (1H, d, J 7.3 Hz, ArH), and 7.62 (1H, br s, NH); m/z (CI$^+$, NH$_a$) 330 (M+1)$^+$.

EXAMPLE 20

2-(4-(E)-(2-(Thien-2-yl)ethenyl)-1,2,3,6-tetrahydropyridin-1-ylmethyl)benzimidazole M.p. 180°–185° C. (dec.) (PhMe); (Found: C, 69.97; H, 5.70; N, 12.45. C$_{19}$H$_{19}$N$_3$S requires C, 70.99; H, 5.96; N, 13.07%); δ$_H$ (DMSO-d$_6$) 2.44 (2H, br s, tetrahydropyridinyl CH$_2$), 2.80 (2H, t, J 5.8 Hz, tetrahydropyridinyl CH$_2$), 3.26 (2H, br s, tetrahydropyridinyl CH$_2$), 3.96 (2H, s, NCH$_2$Ar), 5.79 (1H, br s, tetrahydropyridinyl 5-CH), 6.62 (2H, s, CH=CHAr), 6.95-6.97 (2H, m, ArH), 7.13-7.15 (1H, m, ArH), 7.22-7.27 (4H, m, ArH), and 7.62 (1H, br s, NH); m/z (CI$^+$, NH$_3$) 322 (M+1)$^+$.

EXAMPLE 21

2-(4-(E)-(2-(Thien-3-yl)ethenyl)-1,2,3,6-tetrahydropyridin-1-ylmethyl)benzimidazole M.p. 216°–218° C. (PhMe); (Found: C, 71.03; H, 5.80; N, 12.97. C$_{10}$H$_{19}$N$_3$S requires C, 70.99; H, 5.96; N, 13.07%); δ$_H$ (DMSO-d$_6$) 2.44 (2H, br s, tetrahydropyridinyl CH$_2$), 2.80 (2H, t, J 5.8 Hz, tetrahydropyridinyl CH$_2$), 3.25 (21H, br s, tetrahydropyridinyl CH$_2$), 3.95 (2H, s, NCH$_2$Ar), 5.78 (1H, br s, tetrahydropyridinyl 5-CH), 6.50 (1H, d, J 16.1 Hz, CH=CHAr), 6.65 (1H, d, J 16.1 Hz, CH=CHAr), 7.15 (1H, d, J 1.7 Hz, ArH), and 7.22-7.29 (6H, m, ArH); m/z (CI$^+$, NH$_3$) 322 (M+1)$^+$.

EXAMPLE 22

2-(4-(E)-2-(Furan-2-yl)ethenyl)-1,2,3,6-tetrahydropyridin-1-ylmethyl)benzimidazole Step 1: 1-(4-Pyridyl)-2-(furan-2-yl)ethene A solution of 4-methylpyridine (15 g, 0.16 mol) in acetic anhydride (100 ml) was treated with 2-furaldehyde (15.5 g, 0.16 mmol) and the mixture heated at reflux for 16 hr. The solvent was evaporated to give a black oil which was treated with water (30 ml) and stirred for 30 mins at room temperature. Ethyl acetate (150 ml) and saturated sodium carbonate (100 ml) were then added and the stirring continued for 30 min. The solvents were decanted to leave a black oily residue which was retained (A). From the decanted solvents the organic phase was separated, dried (Na$_2$SO$_4$) and evaporated to give a black oil (B). The oily residue (A) was dissolved in dichloromethane (150 ml), washed with saturated sodium carbonate solution (100 ml), dried (Na$_2$SO$_4$) and evaporated to give a black oil which was combined with oil (B). The mixture was chromatographed on silica gel with a gradient of ethyl acetate in hexane (50%–100%) as eluant to afford the title compound as a brown solid (9.8 g, 36%); δ$_H$ (DMSO-d$_6$) 6.58-6.64 (1H, m, furanyl H), 6.66-6.72 (1H, m, furanyl H), 6.96 (1H, d, H 17.5 Hz, CH=CH), 7.42 (1H, d, J 17.5 Hz, CH=CH), 6.50-6.58 (2H, m, pyridyl H), 7.78-7.82 (1H, m, furanyl H), and 8.50-8.51 (2H, m, pyridyl H).

Step 2: 2-(4-(E)-(2-Furan-2-yl)ethenyl)-1,2,3,6-tetrahydropyridin-1-ylmethyl)benzimidazole A solution of 1-(4-pyridyl)-2-(furan-2-yl)ethene (625 mg, 3.65 mmol) in anhydrous dimethylformamide (10 ml) was treated with 2-chloromethylbenzimidazole (671 mg, 4.02 mmol). The reaction mixture was stirred at reflux for two hours. The solvent was evaporated and the residue redissolved in absolute ethanol (50 ml). Sodium borohydride (174 mg, 4.56 mmol) was added and the mixture stirred at reflux for 40 mins. The solvent was evaporated and the residue partitioned between dichloromethane and water. The organic phase was separated, dried (MgSO$_4$) and evaporated. The residue was chromatographed on silica gel using 97:3:1 dichloromethane/methanol/ammonia as eluant to afford the title compound (148 mg, 13%) as a colourless solid, m.p. 193°–195° C.; (Found: C, 73.37; H, 6.14; N, 13.15. $C_{19}H_{19}N_3O.0.25H_2O$ requires C, 73.64; H, 6.34; N, 13.56%); $\delta_H$ (DMSO-d$_6$) 2.28-2.36 (2H, m, tetrahydropyridinyl CH$_2$), 2.67 (2H, t, J 5.7 Hz, tetrahydropyridinyl CH$_2$), 3.14-3.22 (2H, m, tetrahydropyridinyl CH$_2$), 3.82 (2H, s, NCH$_2$Ar), 5.85-5.94 (1H, m, tetrahydropyridinyl CH), 6.34 (1H, d, J 16.1 Hz, CH=CH), 6.42-6.45 (1H, m, furan 4-H), 6.47-6.52 (1H, m, furan 3-H), 6.68 (1H, d, J 16.2 Hz, CH=CH), 7.10-7.18 (2H, m, 5-H and 6-H), 7.42 (1H, d, J 6.9 Hz, 7-H), 7.55 (1H, d, J 7.0 Hz, 4-H), 7.59 (1H, d, J 1.3 Hz, furan 5-H), and 12.30 (1H, s, NH); m/z (CI$^+$, NH$_3$) 306 (M+1)$^+$.

EXAMPLE 23

2-(4-(E)-(2-(5-Methylfuran-2-yl)ethenyl)-1,2,3,6-tetrahydropyridin-1-ylmethyl)benzimidazole 1-(4-Pyridyl)-2-(5-methylfuran-2-yl)ethene was prepared in the same manner as 1-(4-pyridyl)-2-(furan-2-yl)ethene described in Example 22, Step 1.

A solution of 4-[2-(5-methylfuran-2-yl)ethenyl]pyridine (1.0 g, 5.41 mmol) in anhydrous dimethylformamide (20 ml) was treated with 2-chloromethylbenzimidazole (1.0 g, 5.95 mmol). The reaction was stirred at reflux for two hours. The solvent was evaporated and the residue redissolved in absolute ethanol (50 ml). Sodium borehydride (251 mg, 6.76 mmol) was added and the mixture stirred at reflux for 40 mins. The solvent was evaporated and the residue partitioned between dichloromethane and water. The organic phase was separated, dried (MgSO$_4$) and evaporated. The residue was chromatographed on silica gel using 97:3:1 dichloromethane/methanol/ammonia as eluant to afford the title compound (500 mg, 30%) as a pale lemon solid, m.p. 191°–193° C.; (Found: C, 75.33; H, 6.32; N, 13.17. $C_{20}H_{21}N_3O$ requires C, 75.21; H, 6.63; N, 13.16); $\delta_H$ (DMSO-d$_6$) 2.25-2.35 (5H, m, CH$_3$ and tetrahydropyridinyl CH$_2$), 2.66 (2H, t, J 5.7 Hz, tetrahydropyridinyl CH$_2$), 3.14-3.20 (2H, m, tetrahydropyridinyl CH$_2$), 3.82 (2H, s, NCH$_2$Ar), 5.82-5.88 (1H, m, tetrahydropyridinyl CH), 6.06-6.10 (1H, m, furan 4-H), 6.22-6.30 (2H, m, CH=CH and furan 3-H), 6.58 (1H, d, J 16.1 Hz, CH=CH), 7.05-7.20 (2H, m, 5-H and 6-H), 7.38-7.60 (2H, m, 4-H and 7-H), and 12.29 (1H, s, NH); m/z (CI$^+$, NH$_3$) 320 (M+1)$^+$.

EXAMPLE 24

(E)-2-(4-[2-(3-Methoxyphenyl)ethenyl]-1,2,3,6-tetrahydropyridin-1-yl)methyl benzimidazole M.p. 202°–204° C. (EtOAc); (Found: C, 76.20; H, 6.48; N, 11.83. $C_{22}H_{23}N_3O$ requires C, 78.49; H, 6.71; N, 12.16%); $\delta_H$ (CDCl$_3$) 2.51 (2H, br s, tetrahydropyridinyl CH$_2$), 2.84-2.88 (2H, m, tetrahydropyridinyl CH$_2$), 3.31 (2H, br s, tetrahydropyridinyl CH$_2$), 3.82 (3H, s, OCH$_3$), 4.02 (2H, s, ArCH$_2$N), 5.82 (1H, br s, tetrahydropyridinyl 5-H), 6.46 (1H, d, J 16.1 Hz, CH=CH), 6.76-6.80 (2H, m, ArH and CH=CH), 6.94 (1H, d, J 2.2 Hz, 2'-H), 7.01 (1H, d, J 7.8 Hz, ArH), 7.21-7.28 (3H, m, ArH), and 7.58 (2H, br s, ArH); m/z (CI$^+$, NH$_3$) 346 (M+1)$^+$.

EXAMPLE 25

2-(4-Phenoxymethyl-1,2,3,6-tetrahydropyridin-1-yl) methyl benzimidazole

M.p. 184° C. (dec.) (PhMe); (Found: C, 75.14; H, 6.47; N, 12.92. $C_{20}H_{21}N_3O$ requires C, 75.21; H, 6.63; N, 13.16%); $\delta_H$ (CDCl$_3$) 2.32 (2H, br s, tetrahydropyridinyl CH$_2$), 2.77 (2H, t, J 5.8 Hz, tetrahydropyridinyl CH$_2$), 3.17 (2H, br s, tetrahydropyridinyl CH$_2$), 3.95 (2H, s, ArCH$_2$N), 4.44 (2H, s, CH$_2$OAr), 5.81 (1H, br s, tetrahydropyridinyl 5-H), 6.91-6.98 (3H, m, ArH), 7.18-7.31 (4H, m, ArH), and 7.58 (2H, br s, ArH); m/z (CI$^+$, NH$_3$) 320 (M+1)$^+$.

We claim:

1. A compound of formula I, or a pharmaceutically acceptable salt thereof:

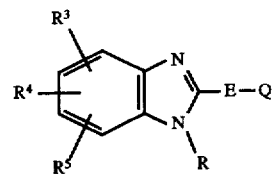

wherein

E represents —CH$_2$— or —CH$_2$CH$_2$—;

R represents hydrogen or C$_{1-6}$ alkyl;

Q represents a group of formula Qa, Qb or Qc:

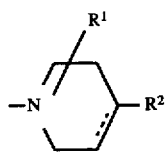 (Qa)

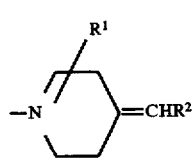 (Qb)

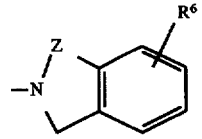 (Qc)

in which the broken line represents an optional chemical bond;

R$^1$ represents hydrogen, or an optionally substituted C$_{1-6}$ alkyl, C$_{1-6}$ alkoxy, C$_{2-6}$ alkenyl, C$_{2-6}$ alkynyl, aryl, aryl (C$_{1-6}$) alkyl, aryl (C$_{1-6}$) alkoxy, aryl (C$_{2-6}$) alkenyl, aryl (C$_{2-6}$) alkynyl, C$_{3-7}$ heterocycloalkyl (C$_{1-6}$) alkyl, heteroaryl, heteroaryl (C$_{1-6}$) alkyl, heteroaryl (C$_{2-6}$) alkenyl or heteroaryl (C$_{2-6}$) alkynyl group;

R$^2$ represents aryl, aryl(C$_{1-6}$)alkyl, aryloxy(C$_{1-6}$)alkyl, aryl(C$_{1-6}$)alkoxy, aryl(C$_{2-6}$)alkenyl, aryl(C$_{2-6}$)alkynyl, heteroaryl or heteroaryl(C$_{2-6}$)alkenyl, any of which groups may be optionally substituted on the aromatic ring;

R$^3$, R$^4$ and R$^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$_b$, —NR$^a$CO$_2$R$^b$, —COR$^a$, —CO$_2$R$^a$ or —CONR$^a$R$^b$;

Z represents —CH$_2$— or —CH$_2$CH$_2$—;

R$^6$ represents hydrogen, C$_{1-6}$ alkyl, C$_{1-6}$ alkoxy, aryl, aryl(C$_{1-6}$)alkyl or halogen; and R$^a$ and R$^b$ independently represent hydrogen, hydrocarbon or a heterocyclic group.

2. A compound as claimed in claim 1 wherein R$^2$ represents aryl, aryl(C$_{1-6}$)alkyl, aryl(C$_{1-6}$)alkoxy, aryl(C$_{2-6}$)alkenyl, aryl(C$_{2-6}$)alkynyl, heteroaryl or heteroaryl(C$_{2-6}$)alkenyl, any of which groups may be optionally substituted on the aromatic ring.

3. A compound represented by formula IIA, and pharmaceutically acceptable salts thereof:

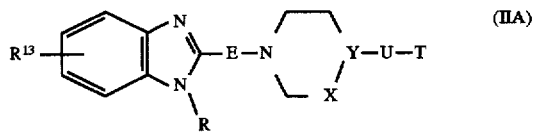
(IIA)

wherein

E and R are as defined in claim 1;

U represents —(CH$_2$)$_n$—, —CH=CH— or —C≡C—;

n is zero, 1, 2 or 3;

—X—Y— represents —CH$_2$—CH— or —CH=C—;

T represents a group of formula (i), (ii), (iii), (iv), (v) or (vi):

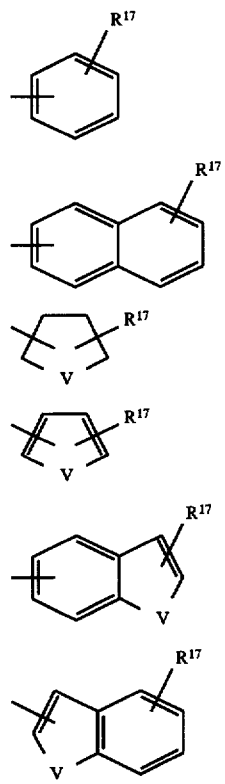

in which V represents oxygen, sulphur or NH; and

R$^{13}$ and R$^{17}$ independently represent hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl (C$_{1-6}$) alkoxy or C$_{2-6}$ alkylcarbonyl.

4. A compound as claimed in claim 1 represented by formula IIB, and pharmaceutically acceptable salts thereof:

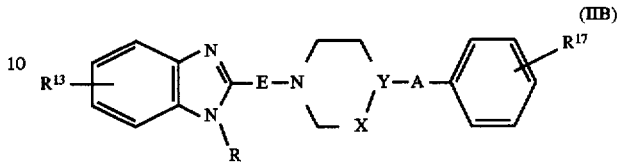
(IIB)

wherein

E and R are as defined in claim 1;

A represents a group of formula —(CH$_2$)$_n$—, —CH=CH—, —C≡C—, —O—(CH$_2$)$_m$— or —(CH$_2$)$_m$—O—;

m is 1, 2 or 3; and n, X, Y, R$^{13}$ and R$^{17}$ are as defined in claim 3.

5. A compound as claimed in claim 4 wherein R represents hydrogen and A represents —C≡C—, —CH=CH— or —O—(CH$_2$)$_m$—.

6. A compound as claimed in claim 1 represented by formula IIC, and salts thereof:

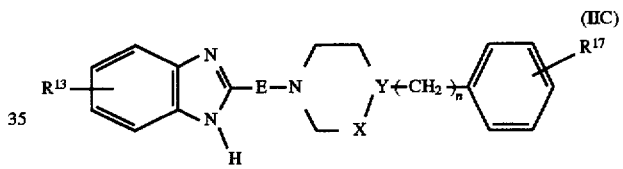
(IIC)

wherein

E is as defined in claim 1; and n, X, Y, R$^{13}$ and R$^{17}$ are as defined in claim 3.

7. A compound as claimed in claim 1 represented by formula IID, and pharmaceutically acceptable salts thereof:

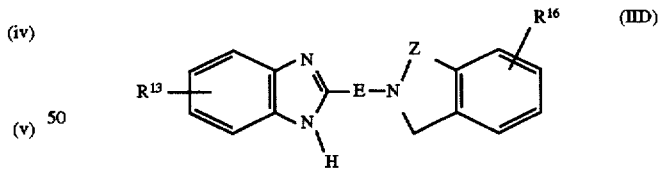
(IID)

wherein

E and Z are as defined in claim 1;

R$^{13}$ is as defined in claim 3; and

R$^{16}$ represents hydrogen, C$_{1-6}$ alkyl, C$_{1-6}$ alkoxy, aryl, aryl(C$_{1-6}$)alkyl or halogen.

8. A compound as claimed in claim 1 represented by formula IIE, and pharmaceutically acceptable salts thereof:

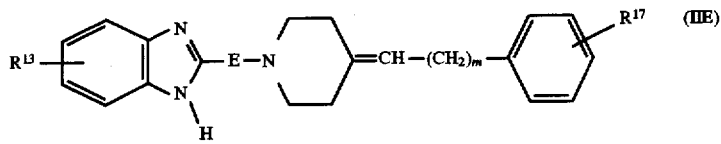

wherein

E is as defined in claim 1;

$R^{13}$ and $R^{17}$ are as defined in claim 3; and m is 1, 2 or 3.

9. A compound as claimed in claim 1 selected from:

2-(1,2,3,4-tetrahydroisoquinolin-2-ylmethyl)benzimidazole;
2-[4-(2-phenylethyl)piperidin-1-ylmethyl]benzimidazole;
2-(4-phenyl-1,2,3,6-tetrahydropyrid-1-ylmethyl)benzimidazole;
5-chloro-2-(1,2,3,4-tetrahydroisoquinolin-2-ylmethyl)benzimidazole;
5-methoxy-2-(1,2,3,4-tetrahydroisoquinolin-2-ylmethyl)benzimidazole;
2-(1,2-dihydroisoindol-2-ylmethyl)benzimidazole;
2-(4-benzylpiperidin-1-ylmethyl)benzimidazole;
2-(4-benzyl-1,2,3,6-tetrahydropyrid-1-ylmethyl)benzimidazole;
2-[4-(3-phenylpropyl)-1,2,3,6-tetrahydropyrid-1-ylmethyl]benzimidazole;
2-[4-(2-phenylethyl)-1,2,3,6-tetrahydropyrid-1-ylmethyl]benzimidazole;
2-[4-(2-phenylethynyl)-1,2,3,6-tetrahydropyrid-1-ylmethyl]benzimidazole;
2-(4-benzyloxy-1,2,3,6-tetrahydropyrid-1-ylmethyl)benzimidazole;
2-[4-(3-phenylpropyl)piperidin-1-ylmethyl]benzimidazole;
2-(4-benzyloxypiperidin-1-ylmethyl)benzimidazole;
2-[4-(3-phenylpropylidene)piperidin-1-ylmethyl)benzimidazole;
2-[4-(E)-(2-phenylethenyl)-1,2,3,6-tetrahydropyrid-1-ylmethyl]benzimidazole;
1-methyl-2-[4-(E)-(2-phenylethenyl)-1,2,3,6-tetrahydropyrid-1-ylmethyl]benzimidazole;
2-[4-(benzothiophen-2-yl)-1,2,3,6-tetrahydropyrid-1-ylmethyl]benzimidazole;
2-[4-(benzofuran-2-yl)-1,2,3,6-tetrahydropyrid-1-ylmethyl]benzimidazole;
2-[4-(E)-(2-(thien-2-yl)ethenyl)-1,2,3,6-tetrahydropyrid-1-ylmethyl]benzimidazole;
2-[4-(E)-(2-(thien-3-yl)ethenyl)-1,2,3,6-tetrahydropyrid-1-ylmethyl]benzimidazole;
2-[4-(E)-(2-(furan-2-yl)ethenyl)-1,2,3,6-tetrahydropyrid-1-ylmethyl]benzimidazole;
2-[4-(E)-(2-(5-methylfuran-2-yl)ethenyl)-1,2,3,6-tetrahydropyrid-1-ylmethyl]benzimidazole;
2-[4-(E)-(2-(3-methoxyphenyl)ethenyl)-1,2,3,6-tetrahydropyrid-1-ylmethyl]benzimidazole;
2-(4-phenoxymethyl-1,2,3,6-tetrahydropyrid-1-ylmethyl)benzimidazole;

and pharmaceutically acceptable salts and prodrugs thereof.

10. A pharmaceutical composition comprising a compound as claimed in claim 1 in association with a pharmaceutically acceptable carrier.

11. A method for the treatment of disorders of the dopamine system, which method comprises administering to a patient in need of such treatment an effective amount of a compound as claimed in claim 1.

* * * * *